US012697193B2

(12) United States Patent
Vollmann et al.

(10) Patent No.: US 12,697,193 B2
(45) Date of Patent: Aug. 4, 2026

(54) METHOD FOR THE PRODUCTION OF A BLANK, BLANK AND A DENTAL RESTORATION

(71) Applicant: DENTSPLY SIRONA Inc., York, PA (US)

(72) Inventors: Markus Vollmann, Gelnhausen (DE); Lothar Volkl, Goldbach (DE); Stefan Fecher, Johannesberg (DE); Carsten Wiesner, Rockenberg (DE)

(73) Assignee: Dentsply Sirona Inc., York, PA (US)

( * ) Notice: Subject to any disclaimer, the term of this patent is extended or adjusted under 35 U.S.C. 154(b) by 0 days.

(21) Appl. No.: 18/382,340

(22) Filed: Oct. 20, 2023

(65) Prior Publication Data

US 2024/0041574 A1 Feb. 8, 2024

Related U.S. Application Data

(62) Division of application No. 15/786,030, filed on Oct. 17, 2017, now Pat. No. 11,833,003.

(30) Foreign Application Priority Data

Oct. 19, 2016 (DE) .......................... 102016119934.6

(51) Int. Cl.
A61C 13/00 (2006.01)
A61C 5/70 (2017.01)
(Continued)

(52) U.S. Cl.
CPC ............ A61C 13/0022 (2013.01); A61C 5/70 (2017.02); A61C 5/77 (2017.02); A61C 13/0006 (2013.01);
(Continued)

(58) Field of Classification Search
CPC ......... A61C 13/0022; A61C 5/70; A61C 5/77; A61C 13/0006
See application file for complete search history.

(56) References Cited

U.S. PATENT DOCUMENTS 4,970,032 A * 11/1990 Rotsaert ................. A61C 13/09
264/20
9,039,947 B2 * 5/2015 Jahns .................... B29C 43/203
264/16
(Continued)

FOREIGN PATENT DOCUMENTS

CA 3038908 A1 4/2018
CA 3162338 A1 4/2018
(Continued)

OTHER PUBLICATIONS

U.S. Appl. No. 15/786,030 U.S. Pat. No. 11,833,003, Oct. 17, 2017, Method for the Production of a Blank, Blank and a Dental Restoration.
(Continued)

*Primary Examiner* — Ralph A Lewis
(74) *Attorney, Agent, or Firm* — SCHWEGMAN LUNDBERG & WOESSNER, P.A.

(57) ABSTRACT

The invention relates to a method for the production of a blank of a ceramic material, wherein a first ceramic material and then a second ceramic material of different compositions are filled into a mold and wherein the materials are pressed and after pressing are sintered. Thereby, a layer of the first ceramic material is filled into the mold, a first open cavity is formed in the layer, the second ceramic material is filled into the first open cavity and the materials are pressed together and are then heat-treated. Both the first ceramic material and the second ceramic material contain, or consists of, lithium silicate glass ceramic.

14 Claims, 5 Drawing Sheets

(51) Int. Cl.

| | | |
|---|---|---|
| *A61C 5/77* | (2017.01) | |
| *A61C 13/08* | (2006.01) | |
| *A61C 13/083* | (2006.01) | |
| *A61C 13/09* | (2006.01) | |
| *A61K 6/818* | (2020.01) | |
| *A61K 6/822* | (2020.01) | |
| *A61K 6/824* | (2020.01) | |
| *A61K 6/833* | (2020.01) | |
| *B29C 43/14* | (2006.01) | |
| *A61C 9/00* | (2006.01) | |
| *B29C 43/20* | (2006.01) | |
| *B33Y 80/00* | (2015.01) | |

(52) U.S. Cl.
CPC .......... *A61C 13/082* (2013.01); *A61C 13/083* (2013.01); *A61C 13/09* (2013.01); *A61K 6/818* (2020.01); *A61K 6/822* (2020.01); *A61K 6/824* (2020.01); *A61K 6/833* (2020.01); *B29C 43/146* (2013.01); *A61C 9/0046* (2013.01); *B29C 2043/147* (2013.01); *B29C 43/203* (2013.01); *B33Y 80/00* (2014.12)

(56) References Cited

U.S. PATENT DOCUMENTS

| | | | | |
|---|---|---|---|---|
| 9,737,465 | B2 * | 8/2017 | Fecher | C03C 4/0021 |
| 11,833,003 | B2 * | 12/2023 | Vollmann | A61C 13/082 |
| 2004/0241464 | A1 * | 12/2004 | de Luca | A61C 13/0022 428/689 |
| 2008/0254414 | A1 * | 10/2008 | McGuire | A61C 13/0022 433/172 |
| 2010/0209876 | A1 | 8/2010 | Sprengart et al. | |
| 2010/0285429 | A1 | 11/2010 | Karim et al. | |
| 2011/0104643 | A1 * | 5/2011 | Giordano | A61C 13/0022 264/16 |
| 2012/0175801 | A1 | 7/2012 | Jahns et al. | |
| 2015/0140274 | A1 * | 5/2015 | Burke | C03C 3/085 264/19 |
| 2015/0173869 | A1 * | 6/2015 | Jung | A61C 13/082 264/16 |
| 2016/0220337 | A1 | 8/2016 | Steger | |
| 2019/0099244 | A1 * | 4/2019 | Vollmann | A61C 13/083 |

FOREIGN PATENT DOCUMENTS

| | | | |
|---|---|---|---|
| CA | 3038908 | C | 8/2022 |
| CA | 3162338 | C | 1/2024 |
| CN | 102573693 | | 7/2012 |
| CN | 103917214 | | 7/2014 |
| CN | 105377216 | | 3/2016 |
| CN | 109843215 | A | 6/2019 |
| DE | 102016119934 | | 5/2018 |
| EP | 3528741 | A1 | 8/2019 |
| EP | 3528741 | B1 | 11/2021 |
| JP | 2015517337 | A | 6/2015 |
| JP | 2015531646 | A | 11/2015 |
| JP | 2016522779 | | 8/2016 |
| JP | 2019534080 | A | 11/2019 |
| JP | 7413017 | B2 | 1/2024 |
| WO | WO-2016104724 | A1 | 6/2016 |

OTHER PUBLICATIONS

"U.S. Appl. No. 15/786,030, 312 Amendment filed Aug. 30, 2023", 7 pgs.

"U.S. Appl. No. 15/786,030, Corrected Notice of Allowability mailed Jul. 25, 2023", 2 pgs.

"U.S. Appl. No. 15/786,030, Corrected Notice of Allowability mailed Nov. 6, 2023", 2 pgs.

"U.S. Appl. No. 15/786,030, Final Office Action mailed Jun. 16, 2022", 33 pgs.

"U.S. Appl. No. 15/786,030, Final Office Action mailed Nov. 24, 2020", 35 pgs.

"U.S. Appl. No. 15/786,030, Non Final Office Action mailed May 27, 2020", 33 pgs.

"U.S. Appl. No. 15/786,030, Non Final Office Action mailed Nov. 17, 2021", 36 pgs.

"U.S. Appl. No. 15/786,030, Notice of Allowance mailed Jul. 6, 2023", 9 pgs.

"U.S. Appl. No. 15/786,030, PTO Response to Rule 312 Communication mailed Oct. 27, 2023", 2 pgs.

"U.S. Appl. No. 15/786,030, Response filed May 1, 2020 to Restriction Requirement mailed Nov. 5, 2019", 9 pgs.

"U.S. Appl. No. 15/786,030, Response filed May 16, 2022 to Non Final Office Action mailed Nov. 17, 2021", 9 pgs.

"U.S. Appl. No. 15/786,030, Response filed May 24, 2021 to Final Office Action mailed Nov. 24, 2020", 9 pgs.

"U.S. Appl. No. 15/786,030, Response filed Oct. 27, 2020 to Non Final Office Action mailed May 27, 2020", 9 pgs.

"U.S. Appl. No. 15/786,030, Response filed Nov. 16, 2022 to Final Office Action mailed Jun. 16, 2022", 11 pgs.

"U.S. Appl. No. 15/786,030, Restriction Requirement mailed Nov. 5, 2019", 6 pgs.

"Canadian Application Serial No. 3,038,908, Office Action mailed Sep. 1, 2021", 4 pgs.

"Canadian Application Serial No. 3,038,908, Response filed Jan. 28, 2022 to Office Action mailed Sep. 1, 2021", 28 pgs.

"Canadian Application Serial No. 3162338, Office Action mailed Jul. 24, 2023", 3 pgs.

"Canadian Application Serial No. 3162338, Response filed Aug. 10, 2023 to Office Action mailed Jul. 24, 2023", 4 pgs.

"European Application Serial No. 17793599.6, Response to Communication pursuant to Rules 161(1) and 162 EPC filed Dec. 3, 2019", 18 pgs.

Kaur, Gurbinder, et al., "Review and the State of the Art: Sol-Gel and Melt Quenched Bioactive Glasses for Tissue Engineering", Journal of Biomedical Materials Research Part B: Applied Biornaterials, vol. 104, No. 6, (2015), 28 pgs.

Li, D., et al., "Effects of Crystal Size on the Mechanical Properties of a Lithium Disilicate Glass-Ceramic", Materials Science and Engineering: A, vol. 669, (Jul. 2016), 8 pgs.

Ritzberger, Christian, "EP2377831 81—Lithium Silicate Glass Ceramic and Glass with Zr02 Content", Google Patents, Google, [Online]. Retrieved from the Internet: <patents.google.com/patent/EP2377831 B1/en?oq=EP-%2B2%2C377%2C831>, (2010), 26 pgs.

Saint-Jean, Simon Jegou, "Dental Glasses and Glass-Ceramics", Advanced Ceramics for Dentistry, (2014), 23 pgs.

"Chinese Application Serial No. 201780064922.0, Notice of Reexamination mailed Mar. 7, 2025", w English translation, 29 pgs.

"Chinese Application Serial No. 201780064922.0, Response filed Jun. 5, 2025 to Notice of Reexamination mailed Mar. 7, 2025", W English Claims, 20 pgs.

"Japanese Application Serial No. 2019-521068, Decision of Rejection mailed Jul. 4, 2023", w/ English Translation, 14 pgs.

"Japanese Application Serial No. 2019-521068, Notification of Reasons for Refusal mailed Jun. 28, 2022", w/ English Translation, 19 pgs.

"Japanese Application Serial No. 2019-521068, Notification of Reasons for Refusal mailed Aug. 3, 2021", w/ English Translation, 16 pgs.

"Japanese Application Serial No. 2019-521068, Notification of Reasons for Refusal mailed Dec. 13, 2022", w/ English Translation, 13 pgs.

"Chinese Application Serial No. 201780064922.0, Decision of Reexamination mailed Jul. 21, 2025", w machine English Translation, 67 pgs.

"Japanese Application Serial No. 2019-521068, Voluntary Amendment filed Jun. 20, 2019", 16 pgs.

"Japanese Application Serial No. 2019-521068, Response filed Feb. 2, 2022 to Notification of Reasons for Refusal mailed Aug. 3, 2021", w current English claims, 14 pgs.

(56)          References Cited

OTHER PUBLICATIONS

"Japanese Application Serial No. 2019-521068, Response filed Aug. 18, 2022 to Notification of Reasons for Refusal mailed Jun. 28, 2022", w current English claims, 11 pgs.

* cited by examiner

1

METHOD FOR THE PRODUCTION OF A BLANK, BLANK AND A DENTAL RESTORATION

THE CROSS-REFERENCE TO RELATED APPLICATIONS

This patent application is a divisional of application Ser. No. 15/786,030 filed Oct. 17, 2017, which claims the benefit of and priority to German Patent Application No. 102016119934.6, filed on Oct. 19, 2016, which are herein incorporated by reference for all purposes.

TECHNICAL FIELD

The invention relates, inter alia, to a method for the production of a blank of a ceramic material, in particular a blank to be used for the production of a dental restoration, wherein a first ceramic material and then a second ceramic material of different compositions are filled into a mold and wherein the materials are pressed and after pressing are sintered.

The invention also relates to a pre-sintered or fully sintered blank for use in producing a dental restoration such as a dental framework, crown, partial crown, bridge, cap, veneer, abutment, pin construction, in particular crown or partial crown, consisting of a ceramic material, that has regions of different compositions.

BACKGROUND OF THE INVENTION

U.S. Pat. No. 8,936,845 B2 discloses a blank of zirconium dioxide that is used for the production of a tooth replacement and comprises a number of layers of different chemical compositions. The individual layers thereby have different percentages of yttrium oxide.

A body of zirconium dioxide exhibits a decrease or increase in chromaticity along a straight line in the L*a*b* color space (US 2014/0328746 AI).

A blank of zirconium dioxide for the production of dental objects in accordance with WO 2014/062375 AI has at least two material regions which have different percentages of tetragonal and cubic crystal phases, wherein in one of the regions the quotient is greater than 1 and in the other region the quotient is lower than 1.

EP 2 371 344 AI relates to a ceramic body which is enriched with a stabilizing agent from the surface to a desired depth.

Lithium disilicate glass ceramics are disclosed in WO 2011/076422 A1 and WO 2012/059143 A1 that are used for the production of dental molded parts. The corresponding glass ceramics are said to have good mechanical and optical properties.

WO 2013/053865 A2 discloses a blank of a lithium silicate glass ceramic from which dental molded parts are produced. It is essential that the ceramic contains a trivalent metal oxide from the group $Y_2O_3$, $La_2O_3$, $Yb_2O_3$, $Bi_2O_3$ and mixtures thereof. Further, the glass ceramic is substantially free of $K_2O$ and $Na_2O$.

One aim of the present invention is to develop a method of the aforementioned type in such a way that a dental restoration can be produced from a ceramic material without laborious finishing, which satisfies esthetic requirements and is of high strength.

SUMMARY OF THE INVENTION

To achieve this aim it is proposed, inter alia, that the first or second, or the first and second ceramic material is one that contains, or consists of, lithium silicate glass ceramic, that a layer of the first ceramic material is filled into the mold, that a first open cavity is formed in the layer, that the second ceramic material is filled into the first open cavity and that the materials are pressed together and are then heat-treated.

In particular the invention relates to a method for the production of a blank of a ceramic material, in particular a blank to be used for the production of a dental restoration, wherein a first ceramic material in powder form and then a second ceramic material in powder form of different compositions are filled into a mold, wherein the materials are pressed and after pressing are sintered, characterized in that a) the first or the second or the first and the second ceramic material used contain, or consist of, lithium silicate glass ceramic, that a layer of the first ceramic material is filled into the mold, b) that a first open cavity is formed in the layer, c) that the second ceramic material is filled into the first open cavity, d) that after filling of the second ceramic material, a second open cavity is formed therein, e) that a third ceramic material is filled into the second open cavity, said third ceramic material has a composition that differs from that of the first and/or second ceramic material, and f) that the materials are pressed together and are then heat-treated.

Alternatively to steps d) and e) a number of first open cavities are formed in the layer of the first ceramic material into which the second ceramic material is filled.

According to the invention, a layer of pourable material is first filled into a mold. This may, for example, be a colorless lithium silicate glass powder that has a grain size in the range 1 to 150 μm, in particular in the range 10 to 30 μm. After the filling with the powder an open cavity is formed, for example by means of a press plunger. This is carried out, for example, by expelling parts of the first ceramic material and/or lightly by compacting the first ceramic material.

The so-formed recess or cavity in particular has a substantially cone-like geometry, which, if a crown or partial crown is to be produced from the blank, can be geometrically aligned with the shape of a tooth stump or an abutment. The second ceramic material is then filled into this cavity or recess and the materials are then pressed together.

There is also the possibility of forming a second open cavity in the second ceramic material that fills the first open cavity. This step can accompany the concomitant pressing of all materials.

Compaction of the materials takes place independently thereof.

Compression/compaction of the ceramic materials filled into the mold is preferably carried out at a pressure between 50 MPa and 400 MPa, in particular between 150 and 350 MPa, especially preferred between 150 and 250 MPa. A density approximately 40-70% of the theoretical density of 2.6 g/cm³ is thereby attained. If binding agents are present, then debinding and pre-sintering or partial sintering are carried out at a temperature between 650° C. and 750° C. for a time period between 10 minutes and 40 minutes.

If a second open cavity is formed in the second ceramic material and a third ceramic material is filled into it, then its composition should differ from that of the second ceramic material, in particular in having a lower translucency than the second/first material.

Independently thereof, the third ceramic material should also consist of, or contain, lithium silicate glass ceramic.

The invention in particular provides for a number of first open cavities to be formed in the layer of the first ceramic material and for the second ceramic material to be filled into them. This yields a number of discrete blank sections, so-called nests, so that after the pre-sintering a number of dental restorations can be derived from the sections of such a blank, in particular through milling and/or grinding. Thereby it is possible for the dimensions of the blank sections to differ from one another to derive restorations of different geometries. The restorations obtained can also differ in the geometric arrangement of the respective root-side/dentin-side material regions. It is therefore possible to obtain teeth of different shapes from one blank, according to the number of nests/blank sections and their geometries. As already mentioned, the dentin cores are formed from the second regions and the incisal regions from the first region.

When a blank having a block-shape geometry is to be produced a single first open cavity is formed in the layer of the first ceramic material. After filling the first open cavity with the second ceramic material a second open cavity is formed and then filled with a third ceramic material, unless the third cavity corresponds to the negative form of an implant connection contour.

Normally the size of such block blank is in the range between 14 mm×14 mm×16 mm and 20 mm×20 mm×20 mm.

When a blank having a disc-like geometry is to be produced several first open cavities are formed in the layer of the first ceramic material and filled with the second ceramic material. If desired after having filled the first open cavities with the second ceramic material in one or more filled first cavities s second open cavity could be formed and filled with the third ceramic material.

A typical size of such a disc is: diameter 80 mm-100 mm, height 10 mm-20 mm.

Furthermore, there is the possibility of coloring the ceramic materials to the desired extent, in particular such that for the first region an incisal material is used which is more translucent and less colored compared to the second ceramic material.

A dental restoration or other molded body is preferably derived from the pre-sintered blank, but there is naturally also the possibility that the blank is first fully-sintered to then produce the molded body, in particular by milling or grinding.

Independently of when the blank is sintered to full density, it is provided in particular that this sintering is to be carried out over a period of between 5 minutes and 120 minutes at a temperature in the range between 750° C. and 950° C. A crystallization firing can be carried out in a number of temperature stages at the same time as the full sintering process or later, for example first crystallization at 600° C. to 670° C. for approximately 10 to 120 minutes, second crystallization at 720° C. to 780° C. for approximately 10 to 60 minutes and a third crystallization firing at 800° C. to 860° C. for approximately 5 to 15 minutes. lithium metasilicate and lithium disilicate crystals are formed as the main crystal phases.

The crystallization firing is preferably carried out after sintering to full density, which is carried out in the liquid phase, i.e., the grains are partly melted.

To produce a dental molded part a blank is used according to the invention that is of compressed lithium silicate glass ceramic powder. To make the glass ceramic powder available, a starting glass is first prepared through melting which has the following composition in percentage by weight:

| | |
|---|---|
| $SiO_2$ | 57.5-60.5% |
| $Li_2O$ | 13.5-20.5% |
| $ZrO_2$ | 8.5-11.5% |
| $P_2O_5$ | 3.0-7.5% |
| $Al_2O_3$ | 0.5-6.0% |
| $K_2O$ | 0.5-3.5% |
| $CeO_2$ | 0.5-2.5% |
| $B_2O_3$ | 0-3% |
| $Na_2O$ | 0-3% |

At least one additive 0-4%.

The starting glass in particular has the following composition in percentage by weight:

| | |
|---|---|
| $SiO_2$ | 57.5-60.5% |
| $Li_2O$ | 14.0-16.0% |
| $ZrO_2$ | 9.0-10.5% |
| $P_2O_5$ | 5.0-6.0% |
| $Al_2O_3$ | 2.5-3.0% |
| $K_2O$ | 1.0-1.5% |
| $CeO_2$ | 0.5-1.0% |
| $B_2O_3$ | 2.5-3.0% |
| $Na_2O$ | 0.1-2.0% |
| $V_2O_5$ | 0.1-0.7% |
| $Er_2O_3$ | 0-1.0% |
| $Y_2O_3$ | 0.3-0.5% |
| $MnO_2$ | 0-0.2% |

The at least one additive is at least one from the group of color pigments and/or fluorescence agents.

Furthermore, the opalescence can be influenced by controlling the crystal formation. The crystals should preferably have a maximum length between 10 nm and 800 nm.

In particular it is provided for the additive to be, or to contain, at least one oxide from the group of rare earth metals.

Optionally binding agents may be added. But their content is not taken into account in the above statement of percentage by weight.

The corresponding mixture of starting materials is then filled into a crucible of fire-resistant material or a noble metal alloy and melted at a temperature between 1350° C. and 1600° C. for a time between 1 and 10 hours, in particular for a time between 4 and 7 hours at a temperature of 1540° C. Homogenization is carried out at the same time, or following on, for example by stirring. The liquid glass so prepared is then quenched in a suitable medium such as a liquid, e.g., water, or high-temperature insulation wool. The quenched glass frit prepared in this way is then dried. It is then milled, for example in a ball mill, and subsequently sieved. Wherein a sieve with a mesh size between 50 and 500 mesh can be used. Where necessary, further milling, for example using a jet mill or attritor mill, can be carried out.

The grains that have a grain size in the region 1 to 150 μm are in particular selected from the glass powder/glass particle powder so prepared.

To allow the blank to be worked without difficulty, without the molded part derived from the blank being unstable upon sintering to full density, either the frit obtained after melting or the pre-milled or finally-milled powder is subjected to a crystallization step. The preferably multi-stage heat treatment referred to in connection with the crystallization firing can be carried out here.

A further heat treatment can then be carried out for relaxation, for example at a temperature between 350 and 500° C. for a time period between 10 and 120 minutes.

The starting materials are selected, to make available a first and/or second ceramic material with the desired color and translucency properties in particular in the form of lithium silicate glass ceramic powder required for the teaching according to the invention. The lithium silicate glass ceramic powder materials prepared as described above are then filled into the mold/press mold according to the teaching of the invention.

In accordance with the teaching of the invention, after sintering to full density a monolithic dental restoration is obtained through material removal, such as the milling or grinding of a blank. The restoration does not necessarily have to be veneered, but if it is, then there is no departure from the invention.

A pre-sintered or fully sintered blank for use in producing a dental restoration such as a dental framework, crown, partial crown, bridge, cap, veneer, abutment, pin construction, in particular crown or partial crown, consisting of a ceramic material, that has regions of different compositions, wherein a first region is of a first ceramic material and at least one second region is of a second ceramic material and the regions are adjacent to each other, is characterized in that the first or the second, or the first and the second ceramic material contains lithium silicate glass ceramic or consists thereof, that at least one second region extends within the first region and has an outer geometry that tapers from a basal region. Thereby, the basal region should extend in the region of an outer surface of the first region, and preferably merge with it.

It is also possible for the second region to have the cavity extending from the basal region.

Independently thereof, the second region in its outer geometry has a cone-like extending geometry.

There is also the possibility that a third region extends within the second region, said third region consisting of a third ceramic material of a composition which differs from that of the second ceramic material.

A feature of this invention and to be emphasized is the fact that a number of second regions are surrounded by the first region, wherein in particular some of the plurality of second regions differ in their external geometries.

Thus, for example, crowns or artificial teeth of different shapes can be produced, which are harder in the dentin than in the incisal region. For this purpose the dentin part of the dental restoration is formed in sections of the second region whereas the incisal part is formed in sections of the first region of the blank.

The invention is further characterized in that the blank is made from a lithium silicate starting glass of the following composition in percentage by weight:

| | |
|---|---|
| $SiO_2$ | 57.5-60.5% |
| $Li_2O$ | 13.5-20.5% |
| $ZrO_2$ | 8.5-11.5% |
| $P_2O_5$ | 3.0-7.5% |
| $Al_2O_3$ | 0.5-6.0% |
| $K_2O$ | 0.5-3.5% |
| $CeO_2$ | 0.5-2.5% |
| $B_2O_3$ | 0-3% |
| $Na_2O$ | 0-3% |

At least one additive 0-4%.

The blank should in particular be prepared from a starting glass that contains the following in percentage by weight:

| | |
|---|---|
| $SiO_2$ | 57.5-60.5% |
| $Li_2O$ | 14.0-16.0% |
| $ZrO_2$ | 9.0-10.5% |

-continued

| | |
|---|---|
| $P_2O_5$ | 5.0-6.0% |
| $Al_2O_3$ | 2.5-3.0% |
| $K_2O$ | 1.0-1.5% |
| $CeO_2$ | 0.5-1.0% |
| $B_2O_3$ | 2.5-3.0% |
| $Na_2O$ | 0.1-2.0% |
| $V_2O_5$ | 0.1-0.7% |
| $Er_2O_3$ | 0-1.0% |
| $Y_2O_3$ | 0.3-0.5% |
| $MnO_2$ | 0-0.2% |

Furthermore, there is the possibility that the ceramic material of the second region is colored and that of the first region is not colored or colored to a lesser degree, so that a higher translucency than in the second region results.

A dental restoration, in particular tooth, crown or partial crown, is characterized by comprising a first layer of a first ceramic material which extends on the incisal side and a root-side-extending second layer consisting of a second ceramic material, in that the first layer has a higher translucency and that the first layer differs in color from the second layer.

BRIEF DESCRIPTION OF THE DRAWINGS

Further details, advantages and features of the invention result not only from the claims and the features disclosed therein—alone and/or in combination—but also from the following description of the example embodiments shown in the drawings.

The following drawings show.

DETAILED DESCRIPTION OF THE INVENTION

Figure 1A:
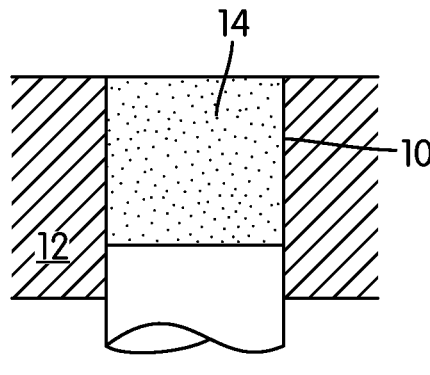
FIG. 1A shows a schematic of a device and process step performed using the device.

The teaching of the invention is illustrated by reference to the figures, in which the same elements are assigned the same reference numerals, wherein in particular dental restorations are produced from a ceramic material having a monolithic structure such that after full sintering an immediately usable monolithic tooth replacement is available.

To this end, the invention provides for the production of a blank, which has regions of ceramic material with differing compositions and thus properties, through which the particular desired optical properties of the restoration to be produced can be attained, which, as mentioned, offer the possibility of immediate usage of the monolithically fabricated tooth replacement after full sintering without, for example, having to apply a incisal layer by hand and firing.

Figure 1B:
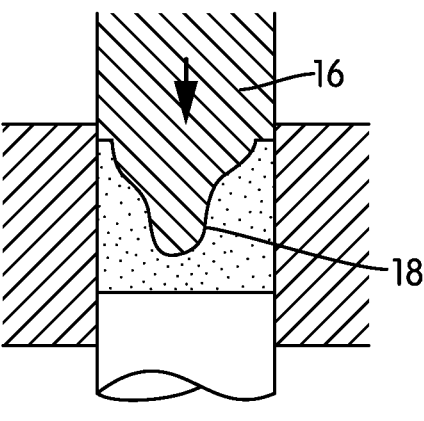
FIG. 1B shows another schematic of the device and process step of the present invention performed using the device shown in FIG. 1A.
Figure 1C:
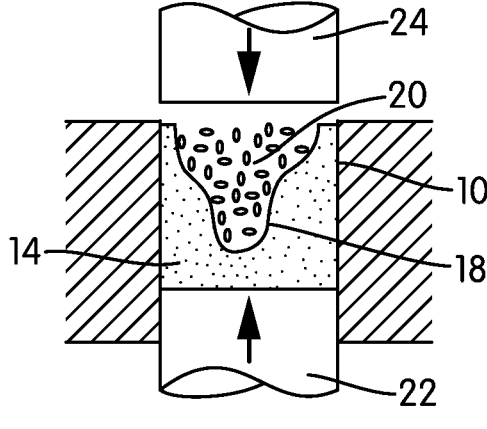
FIG. 1C shows another schematic of the device and process step of the present invention performed using the device shown in FIG. 1B.
Figure 2:
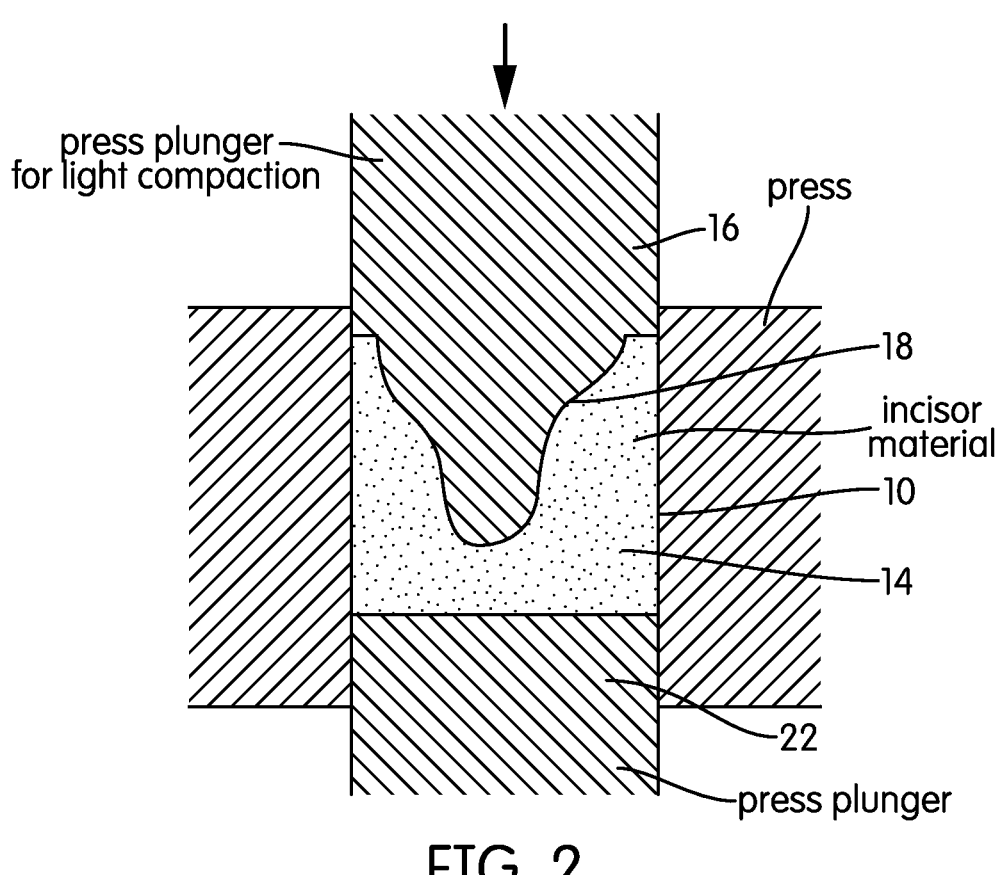
FIG. 2 shows FIG. 1A in greater detail.
Figure 3:
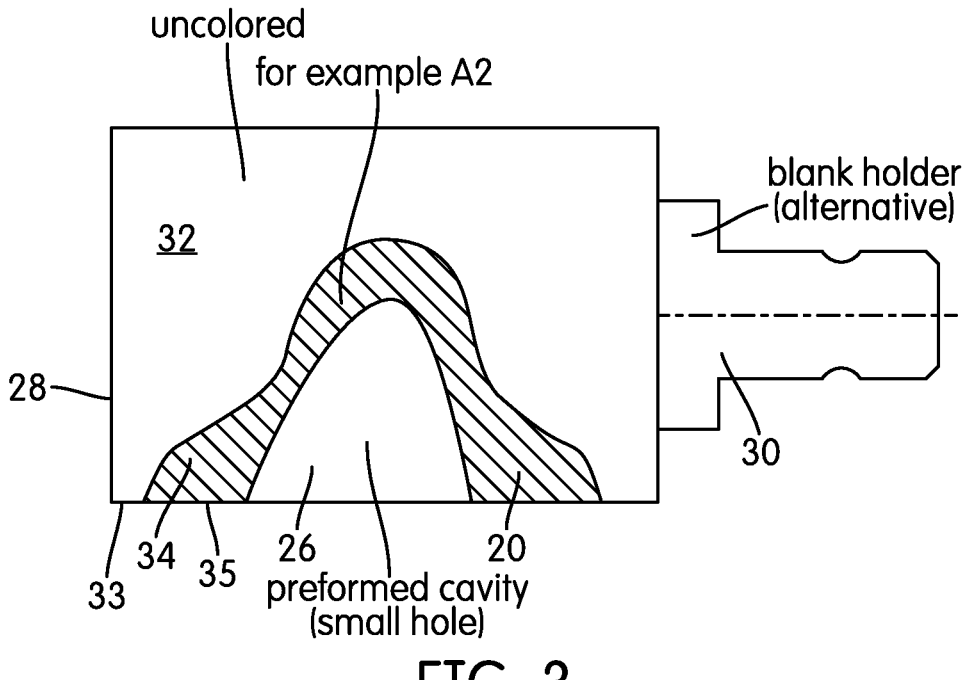
FIG. 3 shows a blank with regions of different material properties.

With reference to FIGS. 1 to 3, the production of a lithium silicate glass ceramic blank will be described from which a dental restoration can be produced, in the example embodiment, a crown. The blank has the shape of a cylinder. Other shapes are possible as cuboids.

Thus a first ceramic material 14 is prepared consisting of lithium silicate glass ceramic. For this a starting glass of the following composition is melted in percentage by weight:

| | |
|---|---|
| $SiO_2$ | 57.5-60.5% |
| $Li_2O$ | 13.5-20.5% |
| $ZrO_2$ | 8.5-11.5% |
| $P_2O_5$ | 3.0-7.5% |
| $Al_2O_3$ | 0.5-6.0% |
| $K_2O$ | 0.5-3.5% |
| $CeO_2$ | 0.5-2.5% |
| $B_2O_3$ | 0-3% |
| $Na_2O$ | 0-3% |

At least one additive 0-4%.

The at least of one additive is at least one from the group of color pigments and/or fluorescence agents. It is in particular provided for the additive to be at least one oxide from the group of rare earth metals or for it to contain such an oxide.

The corresponding mixture of starting materials is then filled into a crucible of fire-resistant material or a noble metal alloy and melted at a temperature between 1350° C. and 1600° C. for a time between 1 and 10 hours, in particular for a time between 4 and 7 hours at a temperature of 1540° C. Homogenization is carried out at the same time, or following on, for example by stirring. The liquid glass so prepared is then quenched in a suitable medium such as a liquid, e.g., water, or high-temperature insulation wool. The quenched glass frit prepared in this way is then dried. It is then milled, for example in a ball mill, and subsequently sieved, wherein a sieve with a mesh size between 50 μm and 250 μm can be used. Where necessary, further milling, for example using a jet mill or Attritor mill, can be carried out.

The grains that have a grain size in the region 1 to 150 μm are in particular selected from the glass powder/glass particle powder so prepared.

To allow the blank to be worked without difficulty, without the molded part derived from the blank being unstable upon sintering to full density, either the frit obtained after melting or the pre-milled or finally milled powder is subjected to a crystallization step. The frit/powder is thereby subject to a preferably multi-stage heat treatment, wherein, for example, a first partial crystallization is carried out from 600° C. to 670° C. for a holding period between 10 minutes and 120 minutes, a second partial crystallization is carried out in the range 730° C. to 780° C. for a holding period between 10 and 60 minutes, and a third partial crystallization step is carried out in the range 800° C. to 860° C. for a time period between 5 minutes and 15 minutes. Where appropriate a further heat treatment can then be carried out for relaxation, for example at a temperature between 350° C. and 500° C. for a time period between 10 and 120 minutes.

It should be noted that crystallization can also be carried out at a later stage, for example after sintering to full density.

The pourable powder or granulate in the form of the first ceramic material 14 is filled into a mold 10 or press mold of a press tool 12.

A binding agent can also be added.

Then, by means of a press plunger 16 an open cavity 18 is formed in the material 14 or in a layer formed from this material. The material 14 is displaced or lightly compacted through the use of the press plunger. Once the cavity 18 is formed (FIG. 1b), the press plunger 16 is removed and a second ceramic material 20 filled into the cavity 18, which largely corresponds in its composition to that of the first material with the limitation that the percentage of coloring substances deviates, so that a desired tooth color is achieved since the dentin of the tooth to be produced is derived from the second ceramic material 20.

After filling of the second ceramic material 20 into the cavity 18 (FIG. 1c), the materials 14, 20, or the layers or regions formed from these, are pressed in the mold 10—by means of a lower or upper punch 22, 24—through which a compaction results. After pressing, the blank 28 has a density of approximately 40-70% of the theoretical density of 2.6 g/cm$^3$. Pressing is preferably carried out at a pressure between 50 MPa and 400 MPa.

FIG. 2 shows the representation of FIG. 1b) in more detail. It can be seen that the cavity 18 is formed through the press plunger 16 in the first ceramic material 14 respectively in the layer comprising that material. On the base side the mold 10 is limited by the press plunger 22.

As can be seen from FIG. 3, a second cavity 26 can be formed in the second material 20 after its compression by the press plunger 22, 24 or optionally after the pre-sintering, for example by milling.

However, it is also possible to form a corresponding second cavity 26 in the material 20, according to FIG. 1c), which completely fills the bottom-side-open cavity 18, by means of a press plunger that is not shown.

Figure 7:
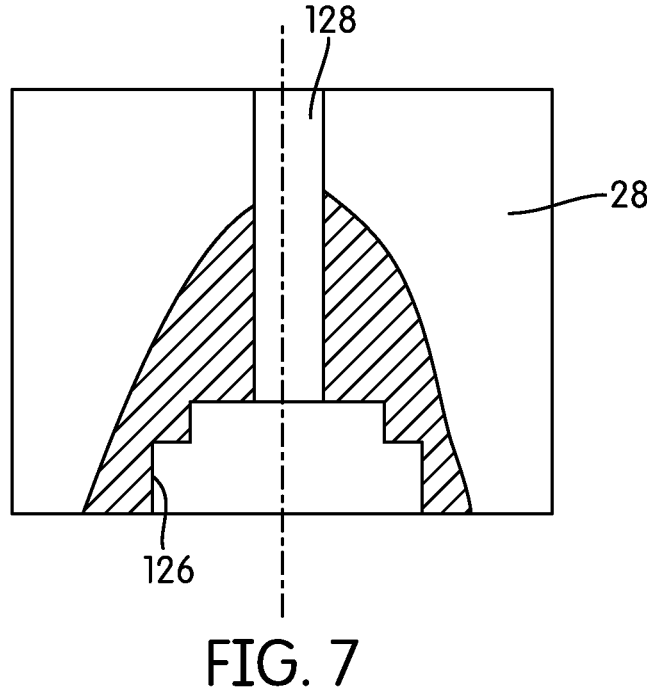
FIG. 7 shows a further embodiment of a blank of the present invention.

Further, there is the possibility to form a recess or a through-hole emanating from the base or in the base of the blank, which, for example, is designed for a function of the dental restoration or which can be used for subsequent working. There is consequently the possibility of providing an opening in the base which exhibits the negative contour of an implant connection. This is illustrated in FIG. 7. Thus FIG. 7 shows a blank 28 that corresponds for example to FIG. 3 that has a three-dimensional layer structure according to the teaching of the invention. As the drawing makes clear, a recess 126 is formed, emanating from the base of the blank 28 in accordance with the invention, corresponding to the negative shape of an implant connection, naturally taking into account the shrinkage behavior of the blank upon sintering. If necessary, a through-opening 128 can also be formed which after production of the molded parts serves as a screw channel. Naturally it is also possible to form the screw channel after sintering of the blank 28 through milling or grinding. An abutment is then formed from the blank 28 in particular through grinding, for which at least the implant connection is already present.

The shaping for the recess 126/128 can be carried out upon pressing of the blank 28, in that the press tool incorporates a mandrel that corresponds to the desired geometry for the recess 126 or 126/128, which in the example embodiment emanates from the press plunger.

Figure 8:
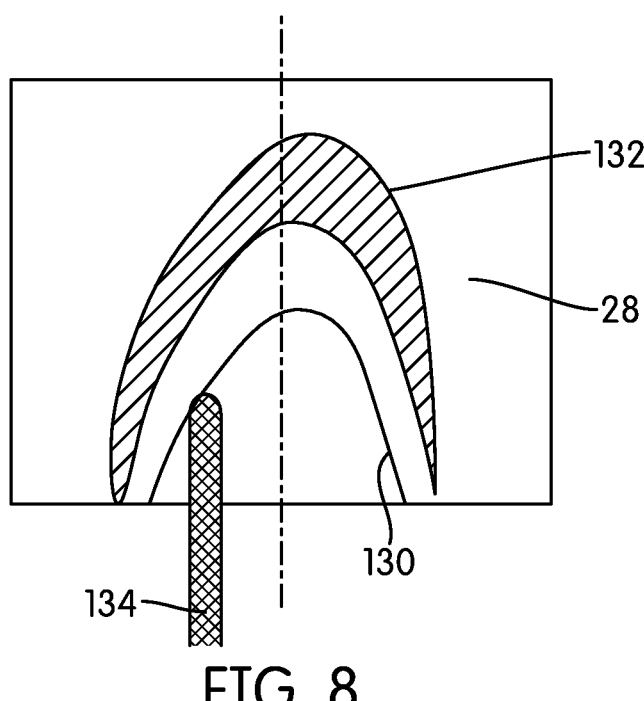
FIG. 8 shows a further embodiment of a blank of the present invention.

FIG. 8 also shows a blank 28, that has a three-dimensional layer structure as described above. A cone-shaped cavity 130 is formed in the blank 28 emanating from the base upon pressing, to facilitate the milling out/grinding of a dental restoration—in the example embodiment a crown 132—and at the same time to insure that wear of the tool 134 used, in particular a ball head milling or grinding tool is reduced compared to the working of blanks that do not have a corresponding cavity. The advantage of the impressed cone-shaped cavity 130 or recess is that upon usage of a spherical-head milling/grinding tool firstly a cone required for the production of the crown 132 no longer has to be created, and moreover, the working is not initially carried out with the center of the ball head; if there is no corresponding cone then the tool must initially work out the cone with the spherical head, primarily with its center, as a result of which there is greater wear.

The cone-shaped cavity 130 can also be formed upon pressing of the blank 28 through the use of a corresponding mandrel in the press tool.

Irrespective of whether the second cavity 26 or a hole or depression, for example for a screw channel or implant connection, is present or not, a sintering of the blank 28 is carried out after pressing at a temperature in particular in the range between 750° C. and 950° C. for a time period between 5 minutes and 120 minutes. There is initially a debinding and then the pre-sintering. The density of the blank 28 after sintering to full density is approximately 2.6 g/cm$^3$ and/or >99.9% of the theoretical final density. The breaking strength of the fully sintered or end-sintered blank 28 is greater than 190 MPa.

The blank 28 is provided with a holder 30, so that the blank 28 can be worked for example in a milling or grinding machine to derive a dental restoration such as a tooth crown from the blank 28, as explained with reference to FIG. 5. Thereby, the tooth crown to be produced is at least virtually laid in the blank 28 such that the incisal region extends into the region 32 formed by the first ceramic material 14 and the dentin region in sections extends into the second region 34 formed by the second ceramic material 20. The blank 28 is then worked taking this data into consideration.

Figure 4:
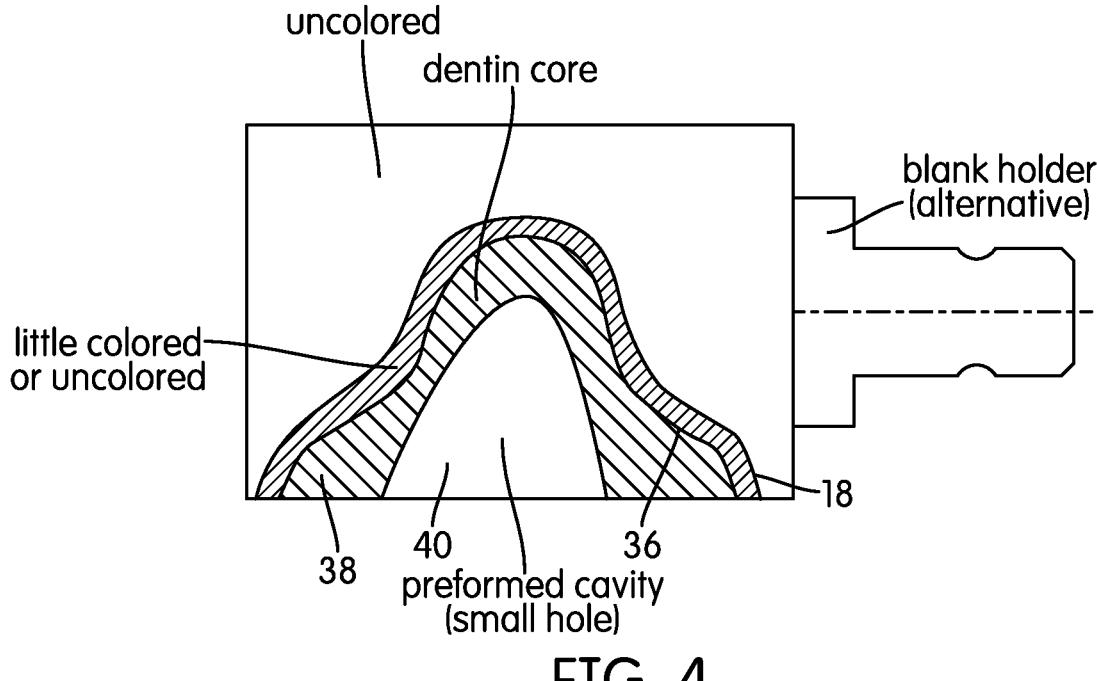
FIG. 4 shows a further blank with regions of different material properties.

FIG. 4 illustrates that after filling of the first cavity 18 in the first ceramic material 14 and filling of the second ceramic material 20 into the cavity 18, optionally a second cavity 36 is formed in accordance with the procedure of FIG. 1*b*), and then a third ceramic material is filled into the cavity 36, which differs from the second ceramic material in its composition such that it has a different color. A cavity 40 may similarly be formed in the third ceramic material 38—as explained with reference to FIG. 3.

Figure 5:
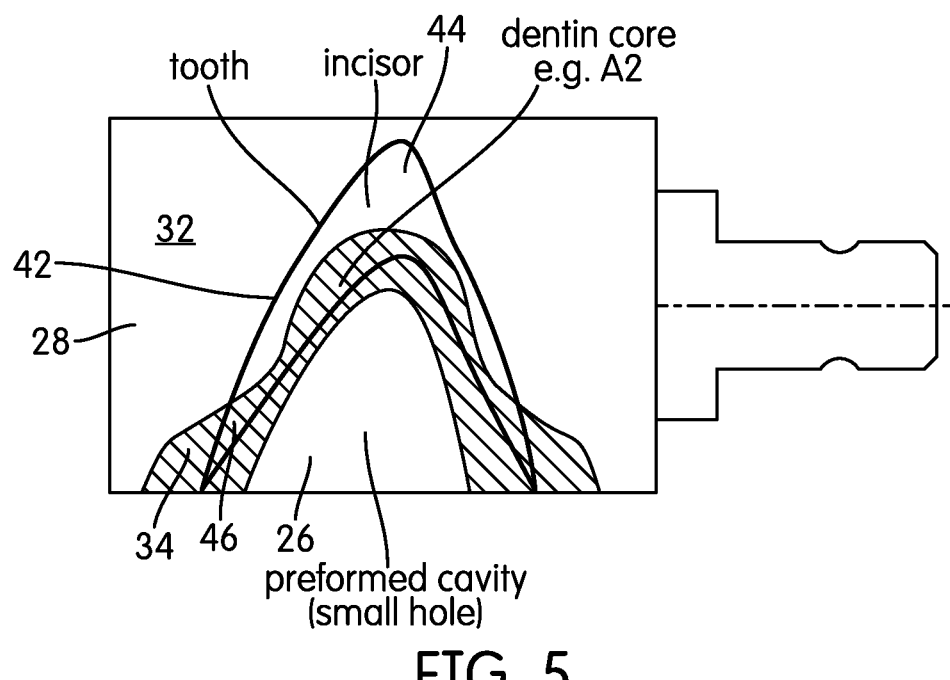
FIG. 5 shows a schematic of a blank with a tooth to be derived therefrom.

As illustrated in FIG. 5, a dental restoration, in the example embodiment, a tooth 42, is derived through working from the blank 28. For this purpose, with knowledge of the course of the first region 32 of the first ceramic material 14 and the second region 34 of the second ceramic material 20 in the blank 28, the tooth 42 to be produced is virtually laid in the regions 32, 34 such that the incisal region extends in the first region 32 and the dentin 46 extends into the second region 34.

After the so virtually positioned tooth 42 is derived through working from the blank 28, a tooth replacement is available, which in principle can be used directly, and in particular does not require any veneering. A monolithic tooth 42 is prepared on the basis of the teaching of the invention. In this case, the production from the blank 28 through working is made easier in that the second region 34 already has an open cavity 26, as described with reference to FIG. 3 and as can be seen from FIG. 5.

Figure 6:
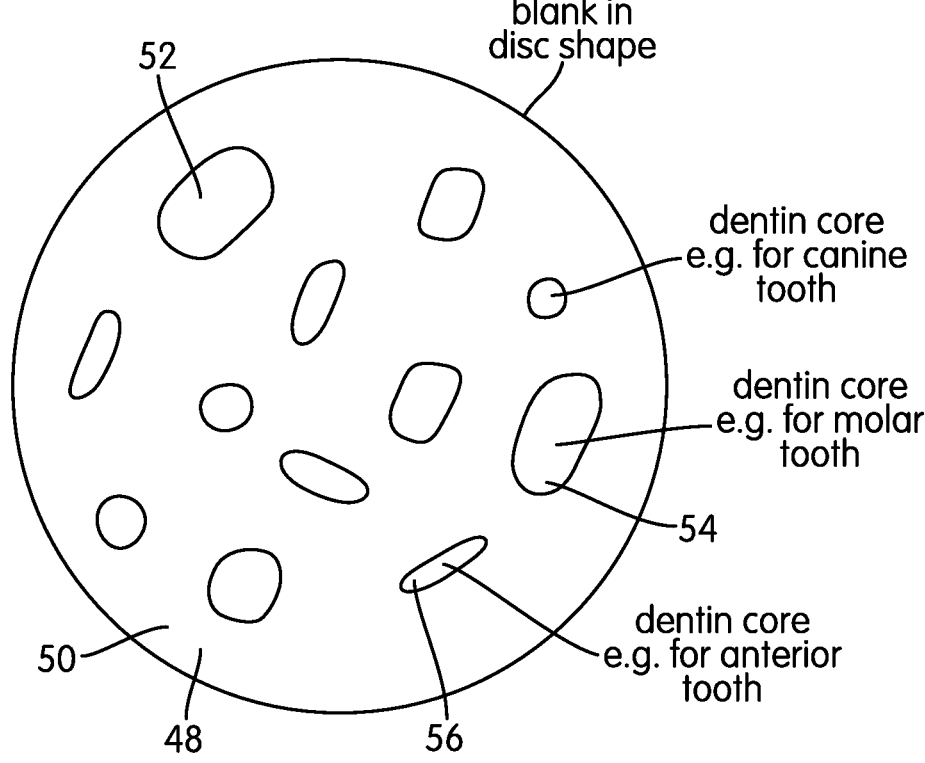
FIG. 6 shows a blank in a top view with a plurality of regions of different material properties.

The teaching of the invention introduces the possibility of forming a blank 48 that has a plurality of regions 52, 54, 56, that are made of the second and optionally a third ceramic material, and can have different geometries (FIG. 6), so that corresponding teeth of different shapes can be formed. The second regions 52, 54, 56 formed from the second ceramic material 20 are embedded in the first ceramic material 48, i.e., are surrounded by this, as illustrated in particular through the Figures. The second regions 52, 54, 56 are uncovered on the base side.

As can be seen in particular from FIGS. 2-4, the second regions have external geometries that taper starting from the bottom, i.e., from the base region 35. It may be referred to as a cone-like geometry, wherein the outer contour represents a freeform surface.

The base region 35/the base surface that limits it on the underside merges with the lower side of the base surface 33 of the first region 32.

To prepare the blank sections 52, 54, 56 also referred to as nests, it is necessary—as described with reference to FIG. 1—to have corresponding open cavities in the layer made of the first material 14 and designated as the first region 50, so that the pourable second ceramic material 20 can be filled into the cavities in the manner described above and then the materials 14, 20 can be pressed together, i.e., compacted.

With regard to the blanks 28, 48 it is to be noted that these can have a cuboid shape, for example with the dimensions 18×15×25 mm or a disk shape, for example with a diameter of 100 mm and height of 15 mm, without thereby limiting the teaching of the invention. This brings in particular—as explained by reference to FIG. 6—the advantage that, for example, a plurality of second regions 52, 54, 56—so-called dentin cores—can be formed in a disk-shaped blank, to obtain not only restorations of different geometries, but also with a favorable layer course with respect to translucency and strength.

Since the position of one or more second regions 52, 56, i.e., the nests, optionally with different geometries, is known, they can be stored in a data record. Then, the restorations to be produced, which are available as CAD data sets, are positioned relative to and in the blank sections so that the tooth replacement can be derived from the blank by milling and/or grinding In other words, teeth of different geometries, for example, can be prepared from a corresponding disc-shaped blank. The schematic clearly shows that the second regions 52, 56 have different dimensions and are intended for dentin cores that have different dimensions.

It was mentioned above that the restorations are derived from the blank that has been pre-sintered or partially sintered, for example through milling, but there is naturally no departure from the invention if the blank is first fully sintered and the tooth replacement then derived. With both embodiments of the invention all advantages resulting from the inventive teaching can be realized.

For the sake of completeness, it is noted that the percentage of lithium silicate crystals in the first and second ceramic materials should lie in the range 10 to 80% by volume. The starting materials may contain compounds which lead to a desired fluorescence and/or coloration.

Thus, for example, $Tb_2O_3/Er_2O_3$ can be used to influence fluorescence and, for example, $MnO$, $Fe_2O_3$, $Y_2O_3$, $V_2O_3$, $CeO_2$ or other rare earth oxides can be used to influence the color.

The amount of lithium disilicate crystals is preferably between 10 to 95 weight percent of the total lithium crystal content. The crystal phase may also include lithium phosphate.

The dentin core designated by the reference numeral 56 is, by way of example, intended for a front tooth and the dentin core designated by the reference numeral 54 is intended for a molar tooth. The not further designated section above the region 54 can be intended for a canine tooth.

The present invention may include one or more of the following features:

Example 1. A method for the production of a blank (28, 48) of a ceramic material, in particular a blank to be used for the production of a dental restoration (42), wherein a first ceramic material (14) in powder form and then a second ceramic material (20) in powder form of different compositions are filled into a mold (10), wherein the materials are pressed and after pressing are sintered, characterized in that the first or the second or the first and the second ceramic material used contain, or consist of, lithium silicate glass ceramic, that a layer of the first ceramic material (14) is filled into the mold (10), that a first open cavity (18) is formed in the layer, that the second ceramic material (20) is filled into the first open cavity (18), and that the materials are pressed together and are then heat-treated.

Example 2. The method according to example 1, characterized in that to produce the first and/or second ceramic material the composition of the starting glass contains, or consists of, in percentage by weight:

| | |
|---|---|
| $SiO_2$ | 57.5-60.5% |
| $Li_2O$ | 13.5-20.5% |
| $ZrO_2$ | 8.5-11.5% |
| $P_2O_5$ | 3.0-7.5% |
| $Al_2O_3$ | 0.5-6.0% |
| $K_2O$ | 0.5-3.5% |
| $CeO_2$ | 0.5-2.5% |
| $B_2O_3$ | 0-3% |
| $Na_2O$ | 0-3% |

At least one additive 0-4%.

Example 3. The method according to example 1, characterized in that to produce the first and/or second ceramic material the composition of the starting glass contains, or consists of, in percentage by weight:

| | |
|---|---|
| $SiO_2$ | 57.5-60.5% |
| $Li_2O$ | 14.0-16.0% |
| $ZrO_2$ | 9.0-10.5% |
| $P_2O_5$ | 5.0-6.0% |
| $Al_2O_3$ | 2.5-3.0% |
| $K_2O$ | 1.0-1.5% |
| $CeO_2$ | 0.5-1.0% |
| $B_2O_3$ | 2.5-3.0% |
| $Na_2O$ | 0.1-2.0% |
| $V_2O_5$ | 0.1-0.7% |
| $Er_2O_3$ | 0-1.0% |
| $Y_2O_3$ | 0.3-0.5% |
| $MnO_2$ | 0-0.2% |

Example 4. The method according to at least one of the above examples, characterized in that a powder with a mean grain size between 1 μm and 150 μm, in particular between 10 μm and 30 μm, is used as the first and/or second ceramic material.

Example 5. The method according to at least one of the above examples, characterized in that the first ceramic material has a composition that differs from the second ceramic material in terms of translucency and/or fluorescence and/or color and/or opalescence.

Example 6. The method according to example 1, characterized in that after filling of the second ceramic material (18), a second open cavity (26, 36) is formed therein.

Example 7. The method according to at least one of the above examples, characterized in that that the third ceramic material (38) consists of, or contains, lithium silicate glass ceramic.

Example 8. The method according to at least one of the above examples, characterized in that a number of first open cavities (18) are formed in the layer of the first ceramic material (14) and into which ceramic material (18), in particular the second ceramic material, is filled.

Example 9. The method according to at least one of the above examples, characterized in that at least some of the plurality of open first cavities (18) have internal geometries that differ from one another.

Example 10. The method according to at least one of the above examples, characterized in that the internal geometry of the first open cavity (18) is geometrically aligned with the course of a dental jaw region to be provided with a restoration, such as a tooth stump, or an abutment that emanates from a jaw region.

Example 11. The method according to at least one of the above examples, characterized in that upon working of the dental restoration out of the blank (28, 48) the dentin region of the dental restoration is formed at least in regions from the second ceramic material (20) and the incisal region is formed from the first ceramic material (14).

Example 12. The method according to at least one of the above examples, characterized in that $Tb_2O_3$ and/or $Er_2O_3$ are added to the starting material to influence fluorescence.

Example 13. The method according to at least one of the above examples, characterized in that to influence the opalescence the crystals of the crystal phase have a maximum length extension of between 10 nm and 800 nm.

Example 14. The method according to at least one of the above examples, characterized in that during pressing a recess is formed in the blank (28) that corresponds to a negative form of an implant connection contour (126).

Example 15. The method according to at least one of the above examples, characterized in that a recess (130) that has a cone-shaped geometry is formed in the blank (28) during pressing, from which the internal cavity of a dental restoration is formed through milling and/or grinding.

Example 16. A pre-sintered or fully sintered blank (28, 48) for use in producing a dental restoration (42) such as a dental framework, crown, partial crown, bridge, cap, veneer, abutment, pin construction, in particular crown or partial crown, consisting of a ceramic material, that has regions of different compositions, wherein a first region (32, 50) is of a first ceramic material (14) and at least one second region (34) is of a second ceramic material (20) and the regions are adjacent to each other, characterized in that the first or the second, or the first and the second ceramic material contains, or consists of, lithium silicate glass ceramic, that the second region (34, 52, 54, 56) extends within the first region (32) and has an outer geometry that tapers from a basal region (35) or base surface.

Example 17. The blank according to example 16, characterized in that the basal region (35)/the base surface of the second region (34) extends in the region of an outer surface (33) of the first region (32), and preferably merges with it.

Example 18. The blank according to example 16 or 17, characterized in that the second region (34) commencing from its basal region (35)/its base surface has a cavity (26).

Example 19. The blank according to at least one of examples 16 to 18, characterized in that the second region (34) has a cone-like geometry on its outer side.

Example 20. The blank according to at least one of examples 16 to 19, characterized in that a third region (38) extends within the second region (34) and consists of a third ceramic material that has a composition that differs from that of the first and/or second ceramic material (14, 20) and in particular contains, or consists of, lithium silicate glass ceramic.

Example 21. The blank according to at least one of examples 16 to 20, characterized in that a plurality of second regions (52, 54, 56) are surrounded by the first region (32, 50).

Example 22. The blank according to at least one of examples 16 to 21, characterized in that at least some of the plurality of second regions (52, 54, 56) differ from one another in their outer geometries.

Example 23. The blank according to at least one of examples 16 to 22, characterized in that the blank (28, 48) is produced of a lithium silicate glass ceramic of the composition that contains, or consists of, the following in percentage of weight:

| | |
|---|---|
| $SiO_2$ | 57.5-60.5% |
| $Li_2O$ | 13.5-20.5% |
| $ZrO_2$ | 8.5-11.5% |
| $P_2O_5$ | 3.0-7.5% |
| $Al_2O_3$ | 0.5-6.0% |
| $K_2O$ | 0.5-3.5% |
| $CeO_2$ | 0.5-2.5% |
| $B_2O_3$ | 0-3% |
| $Na_2O$ | 0-3% |

At least one additive 0-4%.

Example 24. The blank according to at least one of examples 16 to 23, characterized in that the blank (28, 48) is produced from lithium silicate starting glass that contains, or consists of, in percentage of weight:

| | |
|---|---|
| $SiO_2$ | 57.5-60.5% |
| $Li_2O$ | 14.0-16.0% |
| $ZrO_2$ | 9.0-10.5% |
| $P_2O_5$ | 5.0-6.0% |
| $Al_2O_3$ | 2.5-3.0% |
| $K_2O$ | 1.0-1.5% |
| $CeO_2$ | 0.5-1.0% |
| $B_2O_3$ | 2.5-3.0% |
| $Na_2O$ | 0.1-2.0% |
| $V_2O_5$ | 0.1-0.7% |
| $Er_2O_3$ | 0-1.0% |
| $Y_2O_3$ | 0.3-0.5% |
| $MnO_2$ | 0-0.2%. |

Example 25. The blank according to at least one of examples 16 to 24, characterized in that the second ceramic material (20) differs from the first ceramic material (14) in coloration, in particular through the addition of at least one oxide from the group $MnO$, $Fe_2O_2$, $Y_2O_3$, $V_2O_3$, $CeO_2$, other rare earth oxides.

Example 26. The blank according to at least one of examples 16 to 25, characterized in that after sintering to full density the restoration (42) produced from the blank (28) has a higher translucency on the incisal side than on the dentin side.

Example 27. The blank according to at least one of examples 16 to 26, characterized in that the blank (28) has a recess or depression (126) on its bottom side that has a geometry of an implant connection contour.

Example 28. The blank according to at least one of examples 16 to 27, characterized in that from the depression (126) a through-opening emanates to form a screw channel.

Example 29. The blank according to at least one of examples 16 to 28, characterized in that the blank (28) on its bottom side has a depression (130) that has a cone-shaped geometry.

Example 30. A dental restoration (42), in particular crown or partial crown, produced according to at least example 1, characterized in that the restoration (42) is of monolithic form and consists of at least one first layer (32) of a first ceramic material (14) extending on the incisal side and a second layer (34) of a second ceramic material (20) extending on the dentin side, wherein the first layer has a higher translucency and the first layer differs from the second layer in its color.

The invention claimed is:

1. A pre-sintered or fully sintered blank for use in producing a dental restoration, the presintered or fully sintered blank is formed from a ceramic material comprising regions of different compositions, wherein a first region is of a first ceramic material and at least one second region is of a second ceramic material, wherein the first and second regions are adjacent to each other, wherein the first or the second ceramic material or the first and the second ceramic materials include lithium silicate glass ceramic, wherein the at least one second region extends within the first region and has an outer geometry that tapers from a basal region or base surface;

wherein the at least one second region commencing from the basal region or base surface has a cone shaped cavity dimensioned to accept a grinding tool.

2. The blank according to claim 1, wherein the basal region or the base surface of the second region extends in the region of an outer surface of the first region and merges with it.

3. The blank according to claim 1, wherein the at least one second region has a cone-like geometry on its outer side.

4. The blank according to claim 1, further comprising a third region that extends within the at least one second region and includes a third ceramic material that has a composition that differs from that of the first ceramic material and/or the second ceramic material, wherein the composition of the third ceramic material includes lithium silicate glass ceramic.

5. The blank according to claim 1, wherein a plurality of second regions are surrounded by the first region.

6. The blank according to claim 5, wherein at least some of the plurality of second regions differ from one another in their outer geometries.

7. The blank according to claim 1, wherein the blank is produced of a lithium silicate glass ceramic of the composition that includes the following in percentage of weight:

$SiO_2$ 57.5-60.5%
$Li_2O$ 13.5-20.5%
$ZrO_2$ 8.5-11.5%
$P_2O_5$ 3.0-7.5%
$Al_2O_3$ 0.5-6.0%
$K_2O$ 0.5-3.5%
$CeO_2$ 0.5-2.5%
$B_2O_3$ 0-3%
$Na_2O$ 0-3%
At least one additive 0-4%.

8. The blank according to claim 1, wherein the blank is produced from lithium silicate starting glass that includes, in percentage of weight:

$SiO_2$ 57.5-60.5%
$Li_2O$ 14.0-16.0%
$ZrO_2$ 9.0-10.5%
$P_2O_5$ 5.0-6.0%
$Al_2O_3$ 2.5-3.0%
$K_2O$ 1.0-1.5%
$CeO_2$ 0.5-1.0%
$B_2O_3$ 2.5-3.0%
$Na_2O$ 0.1-2.0%
$V_2O_5$ 0.1-0.7%
$Er_2O_3$ 0-1.0%
$Y_2O_3$ 0.3-0.5%
$MnO_2$ 0-0.2%.

9. The blank according to claim 1, wherein the second ceramic material differs from the first ceramic material in coloration, and includes the addition of at least one rare earth oxide.

10. The blank according to claim 9, wherein the rare earth oxide comprises $MnO$, $Fe_2O_2$, $Y_2O_3$, $V_2O_3$, and/or $CeO_2$.

11. The blank according to claim 1, wherein after sintering to frill density the restoration produced from the blank has a higher translucency on an incisal side than on a dentin side.

12. The pre-sintered or fully sintered blank of claim 1, wherein the cone shaped cavity is dimensioned to accept a spherical ball head grinding tool.

13. A pre-sintered blank for use in producing a dental restoration, wherein the pre-sintered blank is formed from a ceramic material comprising regions of different compositions, wherein a first region is of a first ceramic material and at least one second region is of a second ceramic material, wherein the first and second regions are adjacent to each other, wherein the first or the second ceramic material or the first and the second ceramic materials include lithium silicate glass ceramic, wherein the at least one second region extends within the first region and has an outer geometry that tapers from a basal region or base surface;

wherein the at least one second region commencing from the basal region or base surface has a cavity; and wherein the cavity includes a cone shaped cavity dimensioned to accept a grinding tool.

14. The pre-sintered blank of claim 13, wherein the cone shaped cavity is dimensioned to accept a spherical ball head grinding tool.

* * * * *